(12) United States Patent
Chen et al.

(10) Patent No.: US 11,007,137 B2
(45) Date of Patent: May 18, 2021

(54) USE OF LACTOBACILLUS PLANTARUM GMNL-6 COMPOSITION FOR SKIN CARE

(71) Applicant: GenMont Biotech Incorporation, Tainan (TW)

(72) Inventors: Yi-Hsing Chen, Tainan (TW); Wan-Hua Tsai, Kaohsiung (TW); Chia-Hsuan Chou, Tainan (TW); Ying-Ju Chiang, Tainan (TW)

(73) Assignee: GENMONT BIOTECH INCORPORATION, Tainan (TW)

( * ) Notice: Subject to any disclaimer, the term of this patent is extended or adjusted under 35 U.S.C. 154(b) by 329 days.

(21) Appl. No.: 15/894,028

(22) Filed: Feb. 12, 2018

(65) Prior Publication Data

US 2019/0247295 A1    Aug. 15, 2019

(51) Int. Cl.
*A61K 8/99* (2017.01)
*A61Q 19/08* (2006.01)
*A61Q 19/00* (2006.01)

(52) U.S. Cl.
CPC ............... *A61K 8/99* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 2004/0185022 A1 | 9/2004 | Rubin | |
| 2005/0089499 A1* | 4/2005 | Moussou | A61K 8/97 424/74 |
| 2005/0196480 A1* | 9/2005 | Sullivan | A61K 8/99 424/780 |
| 2008/0107699 A1* | 5/2008 | Spigelman | A01N 63/00 424/404 |
| 2009/0232785 A1* | 9/2009 | Breton | A61K 8/922 424/93.44 |
| 2009/0324563 A1* | 12/2009 | Muroyama | A61K 8/0216 424/93.45 |
| 2010/0226892 A1* | 9/2010 | Gueniche | A61K 8/99 424/93.3 |
| 2012/0282675 A1* | 11/2012 | Kim | A61K 35/747 435/252.9 |
| 2013/0052171 A1* | 2/2013 | Chang | C12R 1/225 424/93.45 |
| 2014/0186409 A1* | 7/2014 | Lang | A61K 8/99 424/400 |
| 2017/0224750 A1* | 8/2017 | Callanan | A61K 35/747 |

FOREIGN PATENT DOCUMENTS

KR    20140128674 A    * 11/2014

OTHER PUBLICATIONS

Almeida et al. Pharmaceutical development and technology, vol. 13, No. 6, pp. 487-494, 2008.*
Yadav et al. "ACNE-Treatment and Prevention", Continental J. Pharmacology and Toxicology Research 1: 1-7, 2007, Wilolud Online Journals, 2007.
Sjerobabski-Masnec et al. "Skin Aging", Acta Clin Croat 2010; 49:515-519, University Department of Dermatoveneregology, Sestre milosrdnice University Hospital, Zagreb, Croatia.
Centers for Disease Control and Prevention, "Skin Infections", Antibiotic Prescribing and Use in Doctor's Offices May 22, 2020, Centers for Disease Control and Prevention.

* cited by examiner

*Primary Examiner* — Vera Afremova
(74) *Attorney, Agent, or Firm* — WPAT, PC

(57) ABSTRACT

The present invention provides a use for probiotic preparing skin care composition, wherein the probiotic comprises *Lactobacillus plantarum* (GMNL-6) with preservation number of BCRC 910777 or CCTCC M 2017765. The composition may be externally-coating drug, pharmaceuticals for external use, care products for external use or cosmetics, and may achieve the effects of improving the skin conditions or aesthetic appearance by promoting secretion of collagen or expression of ceramide synthase.

8 Claims, 6 Drawing Sheets collagen amount of ceramide synthase

USE OF LACTOBACILLUS PLANTARUM GMNL-6 COMPOSITION FOR SKIN CARE

BACKGROUND OF THE INVENTION

Field of the Invention

The present invention relates to *lactobacillus* isolate for using in the field of skin care.

Description of the Prior Art

Currently probiotics products emphasizing in skin use are relatively limit. The probiotics applications on the skin as indicated in the retrospective literature are characterized by two ways: one is applying directly the probiotics to the affected area, which can affect local immune reaction or inhibit directly the growth of harmful bacteria in skin; the other is by oral administration for affecting the intestinal bacteria phase and immune reaction, and further affecting the changes of the skin in distal end after the probiotics reaching the intestinal tract (Jeong J H et al, 2016).

For example, the application on improving or preventing atopic dermatitis (AD) by oral administration of probiotics is widely spread. In retrospective studies (Baquerizo Nole K L et al, 2014, Fuchs-Tarlovsky V et al, 2016, Jeong J H et al, 2016) showed that some *lactobacillus* secret metabolism products, for instance, acetic acid, lactic acid, diacetyl, sphingomyelin phospholipase, hyaluronic acid .etc and/or surface substance to achieve the effects of promoting skin health. Specifically, skin-used probiotics mainly have the following aspects of effects, including acne inhibition (Kim J, Ko Y et al, 2010), UV light damage prevention (Ra J et al, 2014), wound healing promotion (Peral M C et al, 2009), and melanin formation inhibition (Chan C F et al, 2014).

There were few literatures about clinical trials of probiotics on the skin health improvement, and such trials were conducted mainly by oral administration while relatively few studies were undertaken on the application of external usage on skin. In one of these literatures, an emulsion prepared from the extract of *Bifidobacterium longum*, had a significant effect on the moisturization of sensitive skin after wiping for 29 days (N=66, female) (Gueniche A et al, 2010), while relative reports about clinical application of *Lactobacillus* spp. are still lacking.

The main function of the collagen in skin is to provide complete water-supplement for the skin, increase the elasticity of the skin and the luster of the surface. Ceramide is a lipid naturally existed among cells of the stratum corneum of the skin in the body, and is the most important component with the highest proportion in the lipid of the stratum corneum. The main function of ceramide is to closely link for remaining the integrity of lipids in the stratum corneum so as to prevent evaporation of moisture and resist foreign germs and damages.

The present invention mainly uses in vitro mode to select the probiotics that stimulate the collagen secretion and ceramide production on human skin fibroblasts, and further uses skin testing equipment to confirm the health-promoting effects of the probiotics lotion on the skin.

SUMMARY OF THE INVENTION

Since above-mentioned probiotics are not widely studied in the field of skin care, it is urgent to seek the probiotics with effective improvement. Since collagen and ceramide have widely used in the discussion of skin conditions and mechanisms, the present trial utilizes the collagen and ceramide to probe into the effects of probiotics on improving the skin care and has then found out *Lactobacillus plantarum* (GMNL-6) capable of possibly improving the skin conditions; further, detects the skin parameter of subjects with VISIA high-order digital skin detector.

The purpose of the present invention is to provide a use of probiotic for preparing skin care composition, wherein the probiotic comprises *Lactobacillus plantarum* (GMNL-6) with preservation number of BCRC 910777 or CCTCC M 2017765.

To achieve above purpose of the invention, the *Lactobacillus plantatrum* (GMNL-6) is a dead thallus.

To achieve above purpose of the invention, the dead thallus is obtained by treating bacteria-containing liquid under high temperature and pressure.

To achieve above purpose of the invention, the composition is an externally-coating medicine, pharmaceutical for external use, care product for external use or cosmetic.

To achieve above purpose of the invention, the composition may further comprises a pharmaceutically or cosmetically acceptable carrier.

To achieve above purpose of the invention, the care product for external use is toner, lotion, skin cream, hydrator, lip balm, beauty fluid mask or facial cleanser.

To achieve above purpose of the invention, the skin care refers to improving the skin conditions or aesthetic appearance.

To achieve above purpose of the invention, the improving skin conditions is through the promotion of collagen secretion or expression of ceramide synthase.

To achieve above purpose of the invention, he skin care is to decrease the number of spots, pores, wrinkles, UV spots or poryphyrins for the skin.

The instant invention provides the improved skin conditions or aesthetic appearance comprising: (1) treating, reducing and/or preventing fine lines or wrinkles; (2) shrinking the size of pores for the skin; (3) improving the thickness, satiation and/or firmness of skin; (4) improving the softness and/or flexibility of skin; (5) improving the color, luster and/or clearness of skin; (6) increasing original collagen and/or the generation of collagen; (7) improving maintenance and remodeling of elastin; (8) improving the texture of skin and/or promotion of restructuring; (9) improving the restoration and/or function of skin barrier; (10) improving the skin profile appearance; (11) restoring the luster and/or brightness of skin; (12) replenishing the essential nutrients and/or components in skin; (13) improving the poor skin appearance caused by menopause; (14) improving the moisture retention of skin; (15) increasing the resilience and/or elasticity of skin; (16) treating, reducing and/or preventing the sagging of skin; (17) reducing the pigment spots; (18) treating, reducing and/or preventing acnes; or any combinations thereof.

To achieve above purpose of the invention, the composition contains $1\times10^7 \sim 1\times10^{11}$ dead bacteria of GMNL-6 per gram.

To achieve above purpose of the invention, the composition preferably contains $1\times10^8 \sim 1\times10^{10}$ dead bacteria of GMNL-6 per gram.

DETAILED DESCRIPTION OF THE PREFERRED EMBODIMENT

Figure 1A:
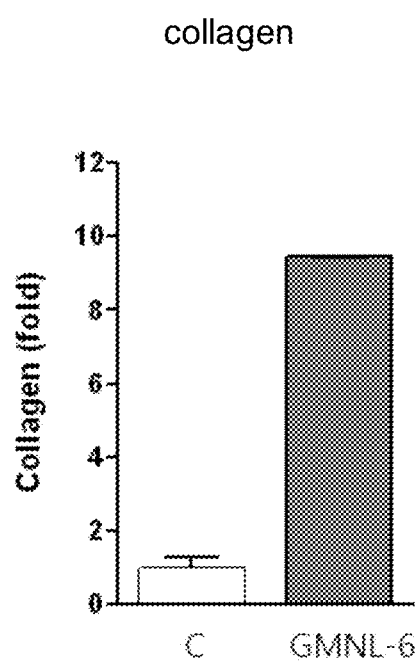
FIG. 1A is a protein expression of collagen

All technical and scientific terms used in this specification, unless otherwise defined, are commonly understood by one of ordinary skill in the art.

The purpose of the present invention is to provide a use of probiotic for preparing skin care composition, wherein the probiotic comprises Lactobacillus plantarum (GMNL-6) with preservation number of BCRC 910777 or CCTCC M 2017765. Also, the present invention relates to a new use for skin care by the composition or the Lactobacillus plantarum, its mechanism is to promote the secretion of collagen and expression of ceramide for achieving the effects of skin care.

Among them, the Lactobacillus plantarum also comprises descedants of its subculture or mutant strains, which however still has the same strain characteristics, genomic or use (for inhibiting enterovirus) according to the present invention.

The composition as set forth herein may comprise, but not limited to: food, beverage, healthy food, animal drinking water additives, animal fodder additives, animal-used and human-used medical compositions, food additives, beverage additives that are suitable for application in the present invention.

The term "pharmaceutically or cosmetically acceptable carrier" means that the substances or compositions must be compatible with other ingredients of the formulation and be harmless to patients.

The term "extract (cell lysate)" may be a single extract obtained by self-determined extraction steps or series-extraction steps, or the extract may also be a combination of several extracts obtained by several independent extraction steps. These combined extracts thus are also contained within the term "extract".

Among them, the pharmaceutically or cosmetically acceptable carrier may comprises one or more agents selected from the following: solvent, emulsifier, suspending agent, decomposer, binding agent, excipient, stabilizing agent, chelating agent, diluent, gelling agent, preservative, lubricant, surfactant and other carriers similar to or suitable for the present invention.

To above compositions, one or more of the dissolution supplements, buffers, preservatives, colorants, spices, flavorings and the like commonly used in the field of above formulations may also be suitably added as needed.

Furthermore, the new strain found in the present invention may also be contained in a composition with the combination of other traditional strains.

For the composition provided by the present invention and the use thereof for skin care, the dosage form thereof may be adjusted as needed, not be limited, preferably being the form of external use on the skin.

The present invention is exemplarily illustrated by but not limited to following embodiments. The pharmaceuticals and biological materials used in the present invention are commercially available and readily available, and the following are only examples of available channels.

The present invention is exemplarily illustrated by but not limited to following embodiments.

Lactobacillus plantarum, which has skin health care efficacy, is selected from the strain database, and the storage number, storage date and strain name of the Lactobacillus plantarum are shown in Table 1.

TABLE 1

Lactobacillus of the present invention in the Bioresource Collection and Research Center (BCRC), Food Industry Research and Development Institute, Hsinchu, Taiwan and China Center for Type Culture Collection, Wuhan, China

| strain name | | storage number | storage date | address |
| --- | --- | --- | --- | --- |
| Lactobacillus plantarum | GMNL-6 | BCRC 910777 | Apr. 14th, 2017 | 331 Shih-Pin Road, Hsinchu, Taiwan 300 |
| Lactobacillus plantarum | GMNL-6 | CCTCC M 2017765 | Nov. 3$^{rd}$, 2017 | Wuhan University, Wuhan 430072 P. R. China |

Embodiment 1. GMNL-6 can Promote Secretion of Collagen and Expression of Ceramide Synthase 1-1 Steps of Preparing Dead Bacteria:

Lactobacillus plantarum (GMNL-6) is inoculated with 1 ml MRS broth from cryo tubes, and incubates at 37° C. for 20 hours under aerobic conditions. The next day, 15 µl of the overnight cultured fluid is inoculated with 1.5 ml MRS broth (1% secondary activation) and incubated at 37° C. for 20 hours under aerobic conditions. Afterward, washing once with PBS and estimating bacteria number with OD 600 nm; and adjusting the number to $1 \times 10^{10}$ cells/ml, and sterilizing under high temperature and pressure on 121° C. for 15 min for preparation.

1-2 Human Skin Fibroblast (Hs68) Cell Mode:

Steps of analyzing collagen of cell culture fluid: Hs68 cells are inoculated into 6 well plate ($2 \times 10^5$ cells/well) overnight, then washing with PBS twice, and replacing with serum free medium while adding GMNL-6 dead bacteria fluid of $1 \times 10^9$ cells/ml for 24 hours' process, then supernatant is collected.

After the supernatant is diluted 10 times, Procollagen type I C-peptide EIA kit (TaKaRa, #MK101) is used to analyze.

Steps of analyzing ceramide synthase genes in the cell (Serine palmitoyltransferase small subunit A, SPTSSA):

Hs68 cells are inoculated into 6 well plate ($2 \times 10^5$ cells/well), washing with PBS twice after overnight and replacing with serum free medium while adding GMNL-6 dead bacteria fluid of $1 \times 10^9$ cells/ml, then the cell extracts are collected after 24 hours' process. Then RNA is extracted and converted into cDNA, and quantitative PCR analysis on ceramide synthase genes (SPTSSA) and house-keeping genes (β-actin).

Figure 1B:
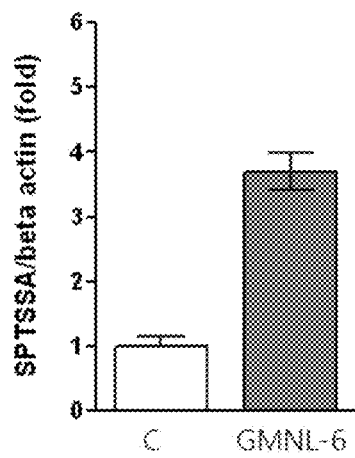
FIG. 1B is a gene expression of ceramide synthase

Experimental Results:

Previously, human skin fibroblasts were in vitro models to screen out Lactobacillus plantarum (L. Plantarum, GMNL-6), which has skin care benefits and ability of promoting secretion of collagen, from dozens of Lactobacillus strains Further, in the same mode, all the experimental results (FIGS. 1A and 1B) have shown that GMNL-6 has both the ability of promoting secretion of collagen and of stimulating the generation of ceramide synthase (SPTSSA) in the cell, and the ceramide synthase is an essential molecule for the synthesis of ceramide in human body while the rise thereof also representing an increase of ceramide creation in the body.

Embodiment 2: *Lactobacillus plantarum* (GMNL-6) Probiotic Emulsion has the Function of Improving the Face Skin 2-1 Experimental Steps:
1. Number of people for experiments: five females (30-40 years old).
2. Evaluation site: Functional cosmetics development and evaluation research center of Jiaonan University of Pharmacy.
3. Before experiments, the facial cleanser is used firstly to clean the face, then the entire face is diagnosed by VISIA high-order digital skin detector and the data is recorded (day 0).
4. During experiments, coating the testing samples after the face is cleaned in the morning and evening on each day (in addition to the emulsion, other maintenance conditions for left and right face remain the same):
 applied on the left face: emulsion of control group (matrix)
 applied on the right face: emulsion of probiotics (matrix+ GMNL-6 dead bacteria)
5. The skin of entire face is diagnosed after four weeks (day 28), the facial cleanser is used firstly to clean the face, then the skin of entire face is diagnosed and the data is recorded.

2-2 Ingredients of Emulsion and Concentration of Probiotics:
1. All ingredients of emulsion (matrix): Water, Polyglyceryl-3/Methyl glucose/Distearate, GlycerylTrioctanoin, Macadamia *Ternifolia* Seed Oil, Propanediol, PEG/PPG/Polybutylene Glycol-8/5/3 Glycerin, Cetyl Alcohol, MyristylMyristate, Glycerin, GlycosylTrehalose/Hydrogenated Starch Hydrolysate, Rice Ferment Filtrate(Sake), *Saccharomyces*/Daylily Flower Ferment Filtrate, Bis-PEG/PPG-20/15 PEG/PPG-20/5 Dimethicone/Methoxy PEG/PPG-25/4 DimethiconeCaprylic/Capric Triglyceride, Sodium Polyacrylate, Phenoxyethanol, o-Cymen-5-ol, Xanthan Gum, Potassium Hydroxide.
2. GMNL-6 concentration in emulsion: $1 \times 10^9$ cells/g emulsion.

2-3 Evaluation Method:
1. Skin detection is conducted by VISIA high-order digital skin detector, and high-resolution pictures of the face is taken through a camera of 12 million pixels and three different light sources (ordinary light, UV light, polarized light), then the skin of certain areas is analyzed by software, thus precisely obtaining skin parameters such as spots, pores, wrinkles, textures, suggillation and poryphyrins to evaluate the potential conditions on the base layer of skin. Further, problems existed in the skin are understood for thus evaluating the data changes before and after using the emulsion. A comparison of qualified data in normal areas obtained from the experimental results in terms of gender and age can serve as an effective evaluation for the products.
2. Through the skin parameters measured by the skin detector on the entire face (comprising: Spots, pores, wrinkles, suggillation and poryphyrins), the difference in score between the left face (emulsion of control group) and the right face (emulsion of probiotics) of each person before use (day 0) and after use (day 28) is evaluated. Calculation formula for score changes is shown as below:

| emulsion of control group (left face) | emulsion of probiotics (right face) |
|---|---|
| $\dfrac{\text{scores after use on left face (day 28)} - \text{scores before use (day 0)}}{\text{scores before use (day 0)}} \times 100\%$ | $\dfrac{\text{scores after use on right face (day 28)} - \text{scores before use (day 0)}}{\text{scores before use (day 0)}} \times 100\%$ |

Figure 2:
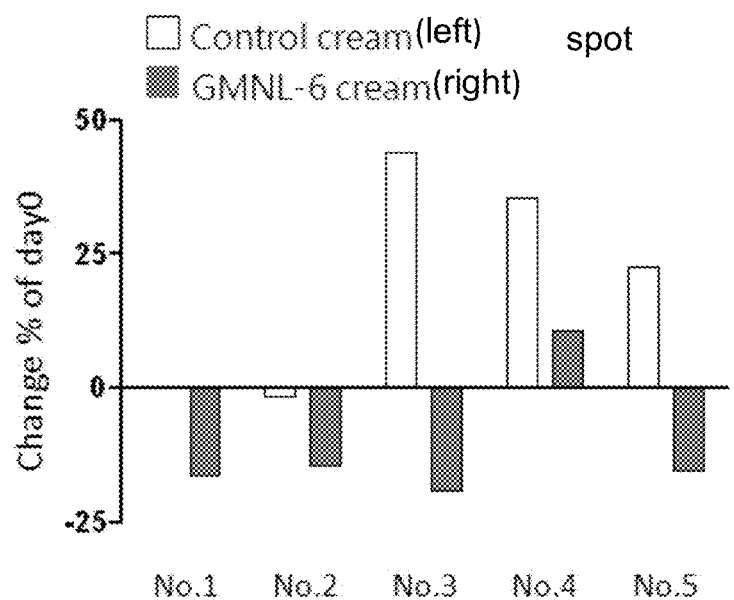
FIG. 2 is the spot number of the subject of VISIA high-order digital skin detector
Figure 3:
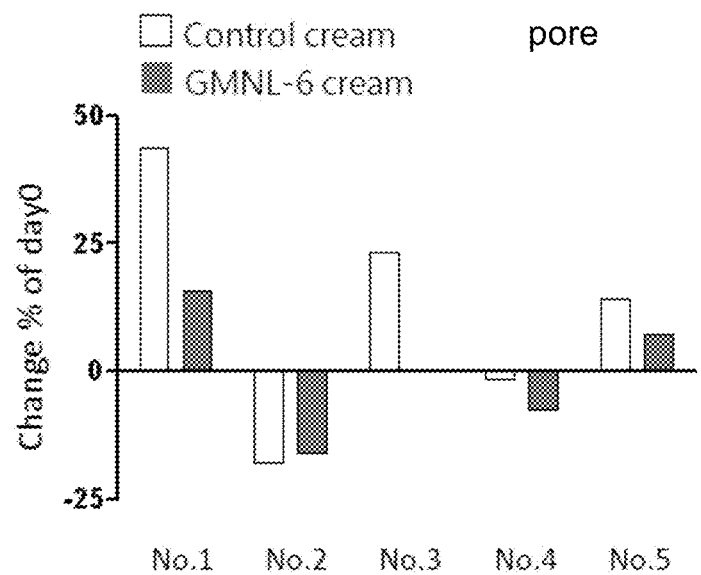
FIG. 3 is the pore number of the subject of VISIA high-order digital skin detector
Figure 4:
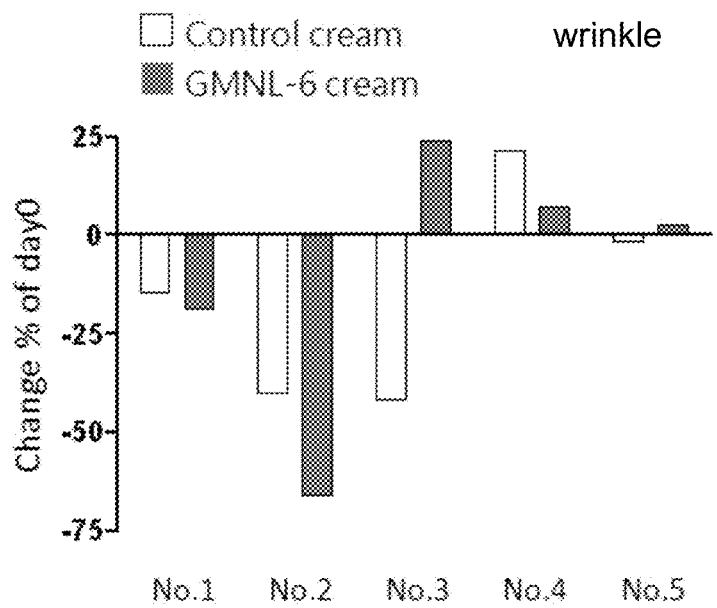
FIG. 4 is the wrinkle number of the subject of VISIA high-order digital skin detector
Figure 5:
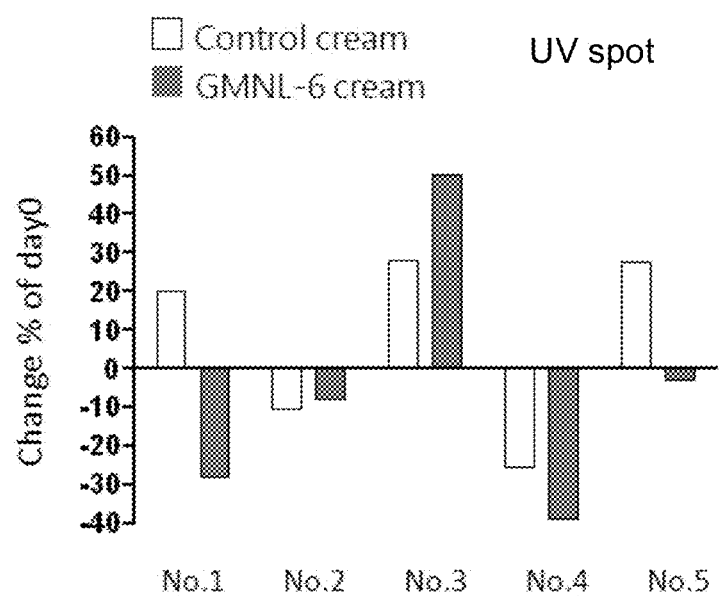
FIG. 5 is the UV spot number of the subject of VISIA high-order digital skin detector
Figure 6:
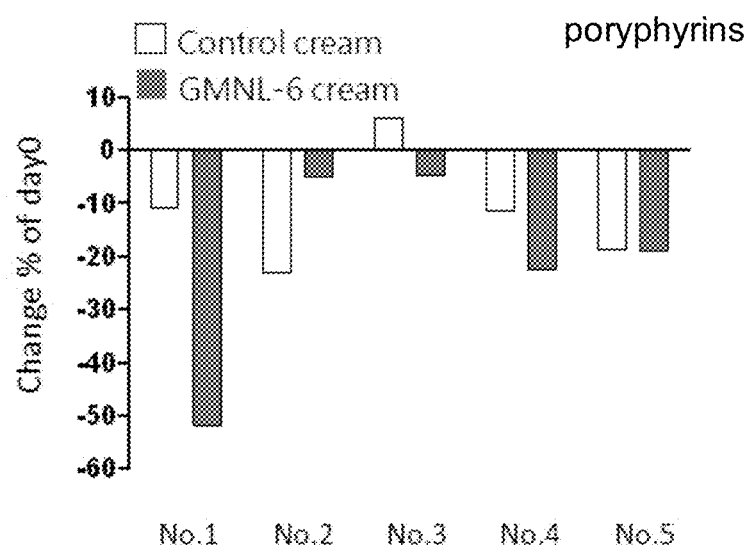
FIG. 6 is the poryphyrins number of the subject of VISIA high-order digital skin detector

※, the percentage represents the degree of difference between the scores after use and before use and compares to determine whether there is improvement through their own left and right sides of the faces, decrease of score changes representing a better skin condition Experimental Results:
The five subjects (NO.1~5) uses emulsion of control group (left face) and emulsion of probiotics (right face) for 28 days, then detected by VISIA high-order digital skin detector for analysis of the skin parameters of these five subjects comprising: Spots (FIG. 2), pores (FIG. 3), wrinkles (FIG. 4), suggillation (FIG. 5) and poryphyrins (FIG. 6). After comparing each person with their own left face, the evaluation of the use of probiotics emulsion group can get better skin improvement data, in each evaluation term at least three or more have been improved, especially for the spots and pores, there are 80 to 100% of the people have been significantly improved. Therefore, on the whole, probiotics have the effects of improving the skin texture, especially in reducing the spots and reducing the pores.

Collagen and ceramide in skin will lose gradually under the influence of age growth or bad habits, so complement and restoration of collagen and ceramide contents in skin is relatively important for the skin care, wrinkle-resistance, anti-UV damage, anti-aging. Through the in vitro experiments, the evaluation from the present invention found that *Lactobacillus plantarum* GMNL-6 can promote the secretion of collagen and the expression of ceramide synthase, representing that GMNL-6 has the special effects on the skin. It can be shown from the human clinical experiments via VISIA high-order digital skin detector that probiotics emulsion of *Lactobacillus plantarum* GMNL-6 have the functions of improving the entire face, which comprise: spots, pores, wrinkles, suggillation and poryphyrins, wherein at least three or more have been improved in terms of each item, especially in terms of fading spots and reducing pores, there are up to 80 to 100% of the people have experienced the effectiveness; in addition, decrease of the poryphyrins means that the growth of acne bacteria is inhibited, thus being somewhat conducive to improving pimples and acnes. Probiotics are mostly applied in human skin clinical studies by oral administration, and there are few clinical studies of adding *Lactobacillus* dead bacteria to the emulsion. And the latter application uses the evaluation method of comparing both left and right faces at the same time, reduces the variability of other skin care products and other individual differences. After four weeks from when five females using GMNL-6 probiotics emulsion, no allergies or any uncomfortable symptoms appear. Therefore, the application of *Lactobacillus plantarum* (GMNL-6) to skin care products is quite safe and has no side effects and should be used as an optimum choice for promoting skin health and preventing skin aging in the future.

The plentiful effects above-mentioned meet the lawful patent requirement for novelty and non-obviousness. The inventor files an application according to law and earnestly urge honorable Office to approve the patent application of the present invention as an encouragement thereof.

What is claimed is:

1. A method of a skin treatment for increasing collagen and ceramide content in the skin and decreasing spots, pores, wrinkles, UV damage and porphyrins of the skin comprising:

administering a probiotic composition comprising *Lactobacillus plantarum* (GMNL-6) with preservation number of BCRC 910777 or CCTCC M 2017765 to an individual in need thereof;

wherein the *Lactobacillus plantarum* (GMNL-6) increases collagen and ceramide content in skin, and decreases spots, pores, wrinkles, ultraviolet light (UV) damage, and porphyrins of the skin.

2. The method according to claim 1, wherein the *Lactobacillus plantarum* (GMNL-6) is a dead bacteria.

3. The method according to claim 2, wherein the dead bacteria is obtained by treating bacteria-containing liquid under high temperature and pressure.

4. The method according to claim 1, wherein the probiotic composition is an externally-coating medicine, pharmaceutical for external use, care product for external use or cosmetic.

5. The method according to claim 1, wherein the probiotic composition may further comprises a pharmaceutically or cosmetically acceptable carrier.

6. The method according to claim 1, wherein the probiotic composition for external use is toner, lotion, skin cream, hydrator, lip balm, beauty fluid mask or facial cleanser.

7. The method according to claim 1, wherein the probiotic composition contains $1 \times 10^7 \sim 1 \times 10^{11}$ dead bacteria of GMNL-6 per gram.

8. The method according to claim 1, wherein the probiotic composition preferably contains $1 \times 10^8 \sim 1 \times 10^{10}$ dead bacteria of GMNL-6 per gram.

* * * * *